(12) United States Patent
Alali

(10) Patent No.: US 11,083,510 B1
(45) Date of Patent: Aug. 10, 2021

(54) SURGICAL WIRE TWISTING TOOL

(71) Applicant: GIFTEDNESS AND CREATIVITY COMPANY, Safat (KW)

(72) Inventor: Ahmad M H M Alali, Safat (KW)

(73) Assignee: GIFTEDNESS AND CREATIVITY COMPANY, Safat (KW)

( * ) Notice: Subject to any disclaimer, the term of this patent is extended or adjusted under 35 U.S.C. 154(b) by 0 days.

(21) Appl. No.: 17/234,076

(22) Filed: Apr. 19, 2021

(51) Int. Cl.
*A61B 17/29* (2006.01)
*A61B 17/56* (2006.01)
*A61B 17/88* (2006.01)
*A61B 17/28* (2006.01)

(52) U.S. Cl.
CPC ........ *A61B 17/8861* (2013.01); *A61B 17/282* (2013.01)

(58) Field of Classification Search
CPC ... A61B 17/8861; A61B 17/282; A61B 17/28; A61B 17/2909; A61B 17/2833; A61B 17/2804; A61B 18/1445; B25B 7/12; B25B 9/00
See application file for complete search history.

(56) References Cited

U.S. PATENT DOCUMENTS

| | | | |
|---|---|---|---|
| 2,032,415 A | 3/1936 | Hirsch | |
| 2,381,703 A | 8/1945 | Slinson | |
| 3,067,748 A | 12/1962 | Straith | |
| 4,050,464 A | 9/1977 | Hall | |
| 5,338,317 A * | 8/1994 | Hasson | A61B 17/2909 600/564 |
| 2009/0157098 A1 | 6/2009 | Meybodi | |
| 2015/0360458 A1* | 12/2015 | Lange | A61F 13/15756 156/226 |
| 2021/0145470 A1* | 5/2021 | Holsten | A61B 17/2909 |

FOREIGN PATENT DOCUMENTS

CA 2510980 A1 12/2006

OTHER PUBLICATIONS

"Pilots HQ Milbar—Reversable Safety Wire Twister Pliers"; printed on Feb. 24, 2021 from https://pilotshq.com/products/milbar-reversable-safety-wire-twister-pliers?gclid=EAlalQobChMlx7egmaKe5AIVAR-GCh2C1gn8EAQYAyABEgLjevD_BWE.
"Sklar TC Corwin Wire Twister 6-1/2""; printed on Feb. 24, 2021 from https://www.medicaldevicedepot.com/Sklar-TC-Corwin-Wire-Twister-6-1-2-p/21-9052.htm.

* cited by examiner

*Primary Examiner* — Tuan V Nguyen
(74) *Attorney, Agent, or Firm* — Nath, Goldberg & Meyer; Richard C. Litman

(57) ABSTRACT

The surgical wire twisting tool includes a hollow housing, a plunger, a rotating member, a jaw actuating rod and a hollow cylindrical guide. A portion of the plunger is received within a second end of the hollow housing, and the rotating member is received within the hollow housing, such that a portion of the rotating member projects through a first end of the hollow housing. A pair of jaws are mounted on one end of the jaw actuating rod. The hollow cylindrical guide is received within the hollow housing, such that the other end of the jaw actuating rod projects through a second end of the rotating member and into the hollow cylindrical guide. The plunger slides through a second end of the hollow cylindrical guide to drive movement of the jaw actuating rod. The pair of jaws may be rotated with respect to the hollow housing, and also locked.

20 Claims, 5 Drawing Sheets

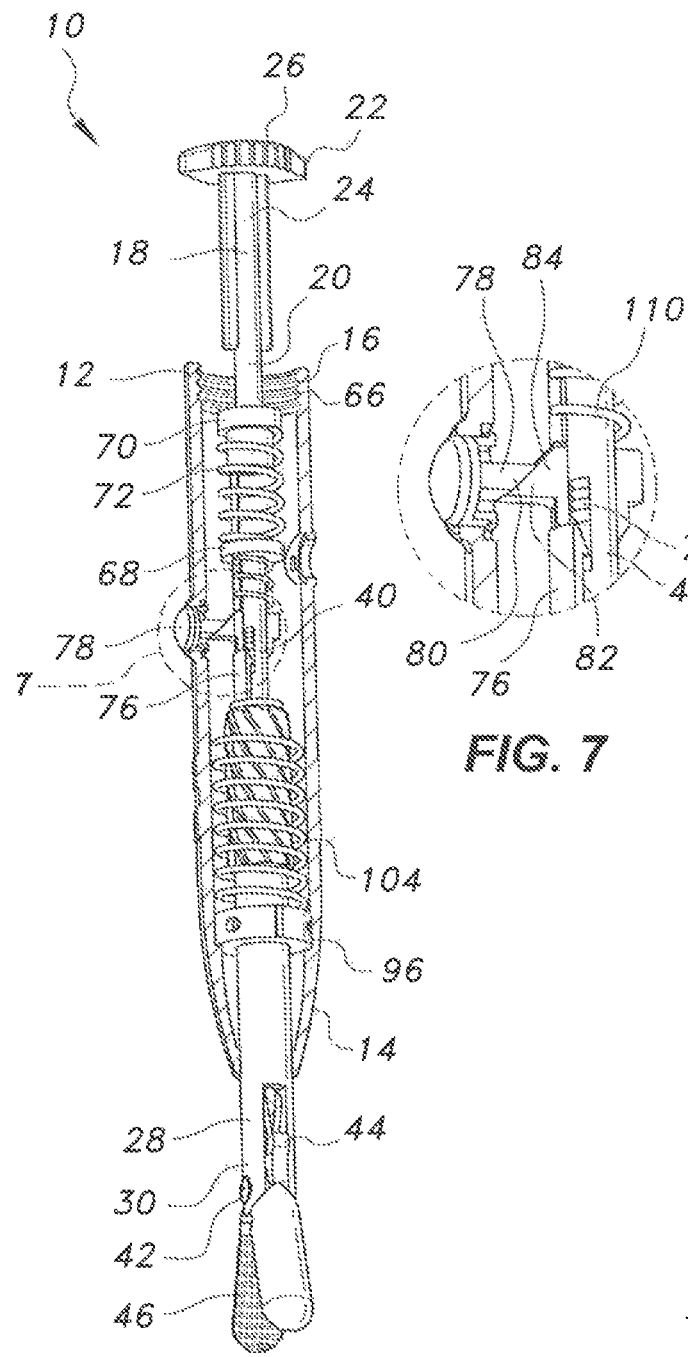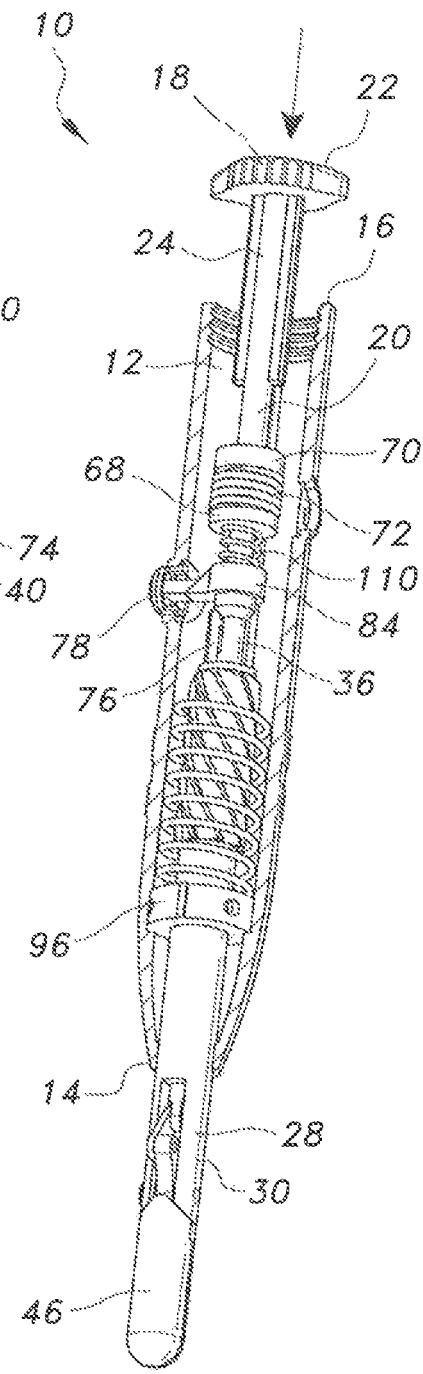
FIG. 5  FIG. 7  FIG. 6

US 11,083,510 B1

SURGICAL WIRE TWISTING TOOL

BACKGROUND

1. Field

The disclosure of the present patent application relates to surgical and medical instruments, and particularly to a surgical tool for both clamping and twisting surgical wire and the like.

2. Description of the Related Art

A wide variety of medical fields use surgical wire, orthodontic wire and the like. For example, wire is used in trauma surgery, general surgery, oral and maxillofacial surgery, orthopedics and orthodontics. Wire twisting is a common technique used in most wire-based applications for stabilizing or approximating different wire segments, including, but not limited to, in fractured bone reduction, maxillomandibular fixation, and wire ligation. The wire is typically held by a conventional pair of locking forceps. The twisting of the wire is a sensitive technique, requiring firm and steady handling of the forceps, and very focused attention on the wire during the twisting, typically by sensing the tightness required and the direction of formation of the twisted wire knot.

Holding the wire steady with conventional forceps while twisting the wrist or finger and being sensitive to the sensation of the twisting and knot formation can be challenging for a surgeon, particularly when the surgeon is manipulating additional surgical apparatus at the same time. Without full and careful control over the wire during twisting, the wire could easily break and/or there could be incorrect or loose proximation of the wire. Thus, a surgical wire twisting tool solving the aforementioned problems is desired.

SUMMARY

The surgical wire twisting tool is a surgical tool for both clamping and twisting surgical wire and the like. The surgical wire twisting tool is configured to allow for one-handed operation by the surgeon. The surgical wire twisting tool includes a hollow housing, a plunger, a rotating member and a jaw actuating rod. A first end of the plunger is slidably received within a second open end of the hollow housing, and the rotating member is received within the hollow housing, such that a first end of the rotating member projects through a first open end of the hollow housing. The rotating member is hollow, such that the jaw actuating rod is at least partially received therein. A pair of jaws are pivotally mounted on a first end of the jaw actuating rod and may be selectively opened and closed.

A hollow cylindrical guide is also received within the hollow housing, such that a second end of the jaw actuating rod projects through a second end of the rotating member and into a first end of the hollow cylindrical guide. The plunger is selectively slidable through a second end of the hollow cylindrical guide to drive sliding movement of the jaw actuating rod with respect to the rotating member. The pair of jaws may be selectively rotated with respect to the hollow housing, and also selectively locked.

These and other features of the present subject matter will become readily apparent upon further review of the following specification.

BRIEF DESCRIPTION OF THE DRAWINGS

FIG. 5 is a partial, partially cut-away perspective view of the surgical wire twisting tool.

FIG. 6 is a partial, partially cut-away perspective view of the surgical wire twisting tool.

FIG. 7 is a cut-away enlarged view of a central portion of the surgical wire twisting tool.

Similar reference characters denote corresponding features consistently throughout the attached drawings.

DETAILED DESCRIPTION OF THE PREFERRED EMBODIMENTS

Figure 1:
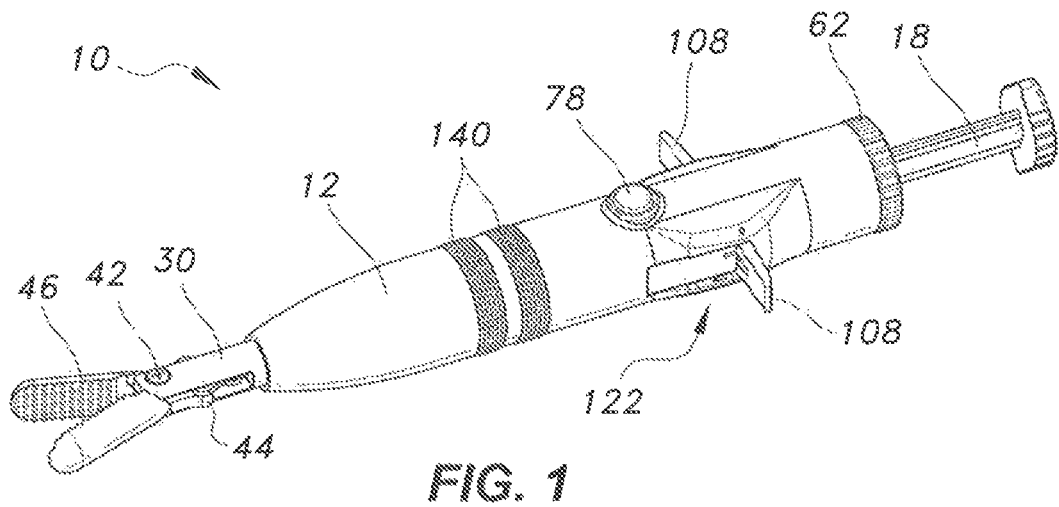
FIG. 1 is a perspective view of a surgical wire twisting tool, with a pair of collapsible wings shown in a deployed position.
Figure 2:
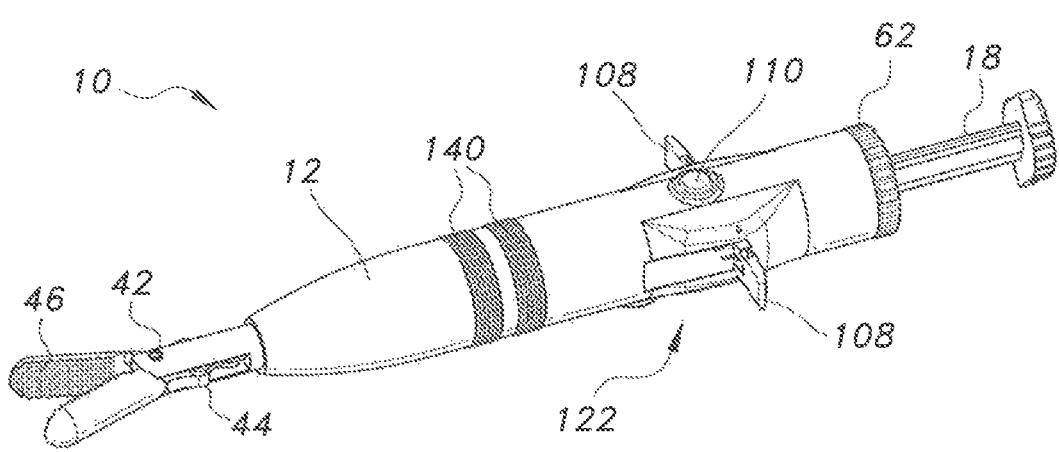
FIG. 2 is a perspective view of an opposite side of the surgical wire twisting tool of FIG. 1.
Figure 3:
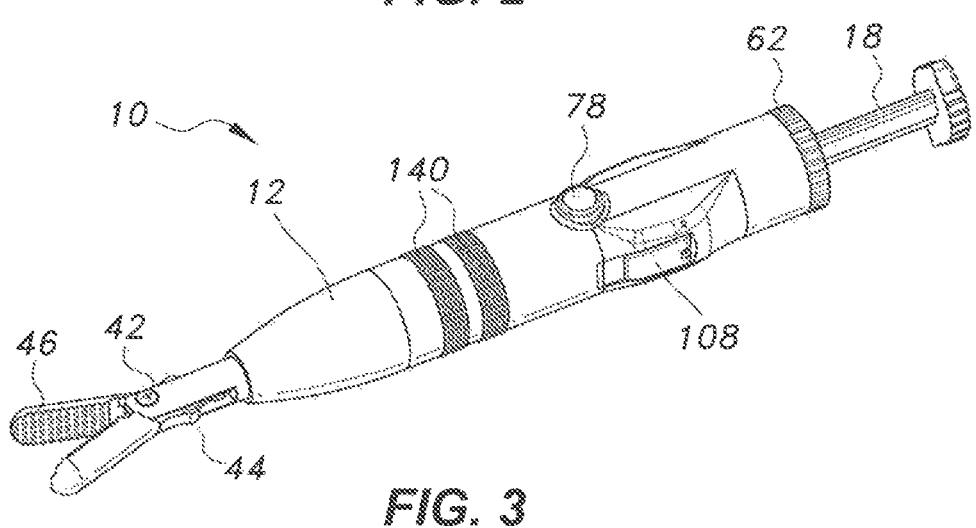
FIG. 3 is a perspective view of the surgical wire twisting tool, with the pair of collapsible wings shown in a collapsed position.

The surgical wire twisting tool 10 is a surgical tool for both clamping and twisting surgical wire and the like. The surgical wire twisting tool 10 is configured to allow for one-handed operation by the surgeon. As shown in FIGS. 1 and 2, the surgical wire twisting tool 10 has a pair of collapsible wings 108, which fold outwardly from compartments 122 formed in the body of a hollow housing 12, providing the surgeon with a pair of finger grips. FIG. 3 shows the pair of collapsible wings 108 folded back into their collapsed or stored position. As will be described in greater detail below, the surgical wire twisting tool 10 has a pair of jaws 46, which may be selectively closed and locked in place to grip surgical wire or the like, in a manner similar to locking surgical forceps, and the jaws 46 may further be driven to rotate in order to twist the surgical wire or the like. The pattern and roughness level of the inner surface of the jaws 46 can vary and can be formed from any suitable material to provide the desired wire grip.

Figure 4:
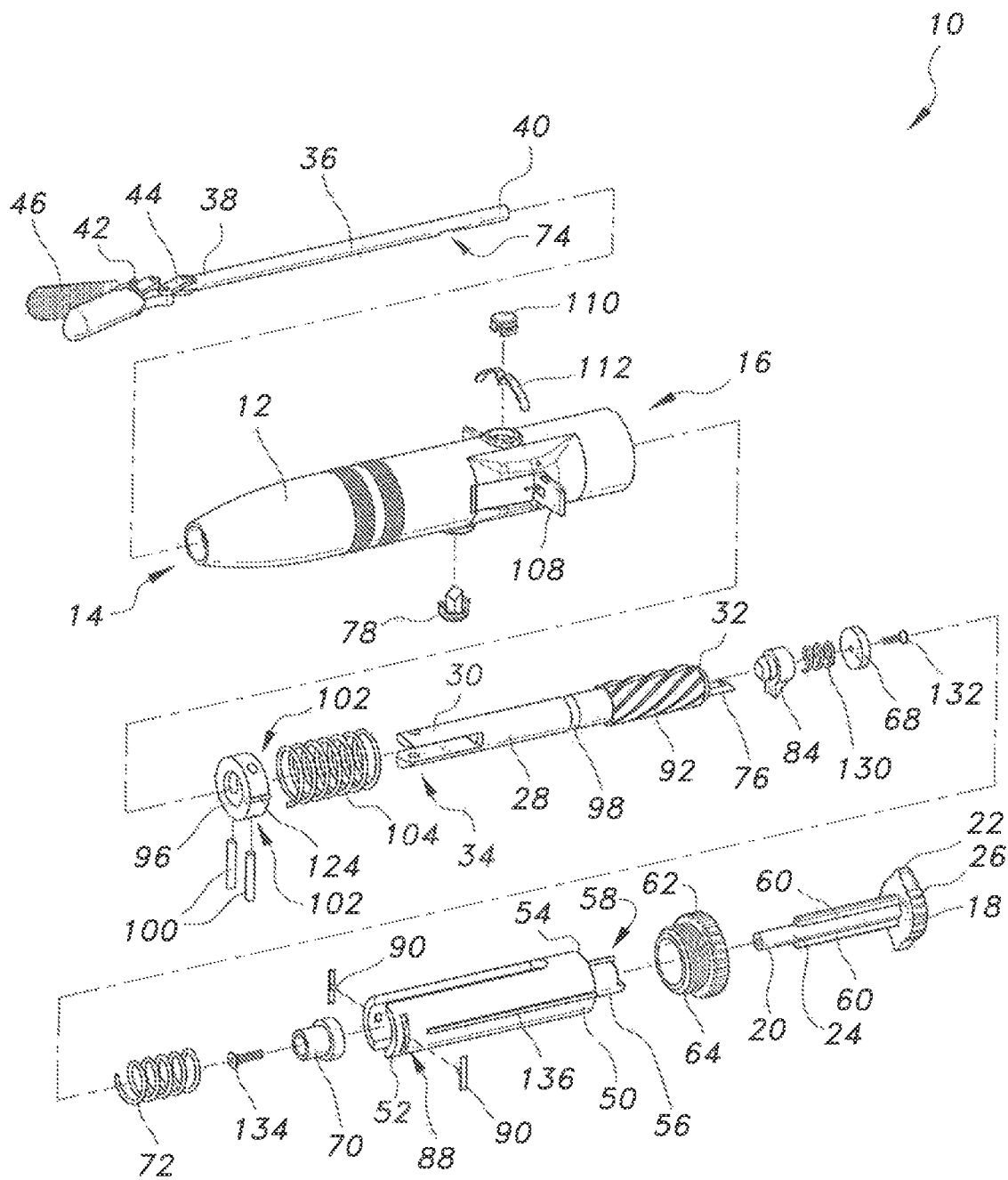
FIG. 4 is an exploded perspective view of the surgical wire twisting tool.
Figure 8:
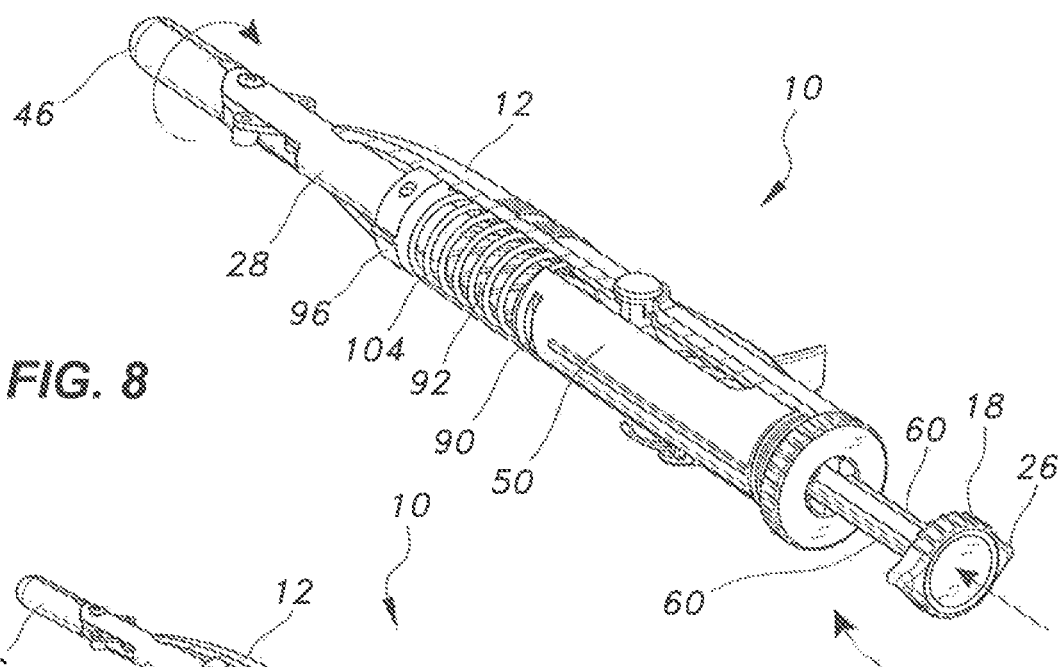
FIG. 8 is a partially cut-away perspective view of the surgical wire twisting tool.

As best seen in FIGS. 4 and 5, the surgical wire twisting tool 10 includes a hollow housing 12 having opposed first and second open ends 14, 16, respectively. It should be understood that hollow housing 12 is shown for exemplary purposes only, and may have any suitable overall shape and relative dimensions. Additionally, it should be understood that the location and patterning of additional gripping material 140 is shown for exemplary purposes only. A first end 20 of a plunger 18 is received within the second open end 16 of hollow housing 12. As shown, plunger 18 may include a rod 24, and a pushing and gripping member 26 may be mounted on a second end 22 of plunger 18. It should be understood that plunger 18 is shown for exemplary purposes only, and may have any suitable overall shape and relative dimensions. A rotating member 28 is also received within hollow housing 12, such that a first end 30 of rotating member 28 projects through first open end 14 of hollow housing 12, as best seen in FIGS. 5 and 6, while a second end 32 of rotating member 28 remains within hollow housing 12. It should be understood that rotating member 28 is shown for exemplary purposes only, and may have any suitable overall shape and relative dimensions.

The rotating member 28 is hollow and receives a jaw actuating rod 36, which has opposed first and second ends 38, 40, respectively. As best seen in FIG. 4, a pair of openings 34 may be formed through first end 30 of rotating member 28 for receiving a bolt 42 or the like. As shown, a four-bar linkage 44 is pivotally secured at one end to the first end 38 of jaw actuating rod 36 and is connected at its other end to a pair of jaws 46, which pivot about bolt 42. Thus, when the ends of bolt 42 are received within openings 34 of rotating member 28, the jaw actuating rod 36 is secured therein. Sliding of the jaw actuating rod 36 back and forth within the rotating member 28 creates a reciprocating folding and unfolding movement of the four-bar linkage 44, thus causing jaws 46 to open and close. It should be understood that four-bar linkage 44 is shown for exemplary purposes only, and that any suitable actuating mechanism for opening and closing jaws 46, driven by the sliding of jaw actuating rod 36, may be used. Further, it should be understood that the pair of jaws 46 is shown for exemplary purposes only and may have any suitable overall shape and relative dimensions.

Figure 9:
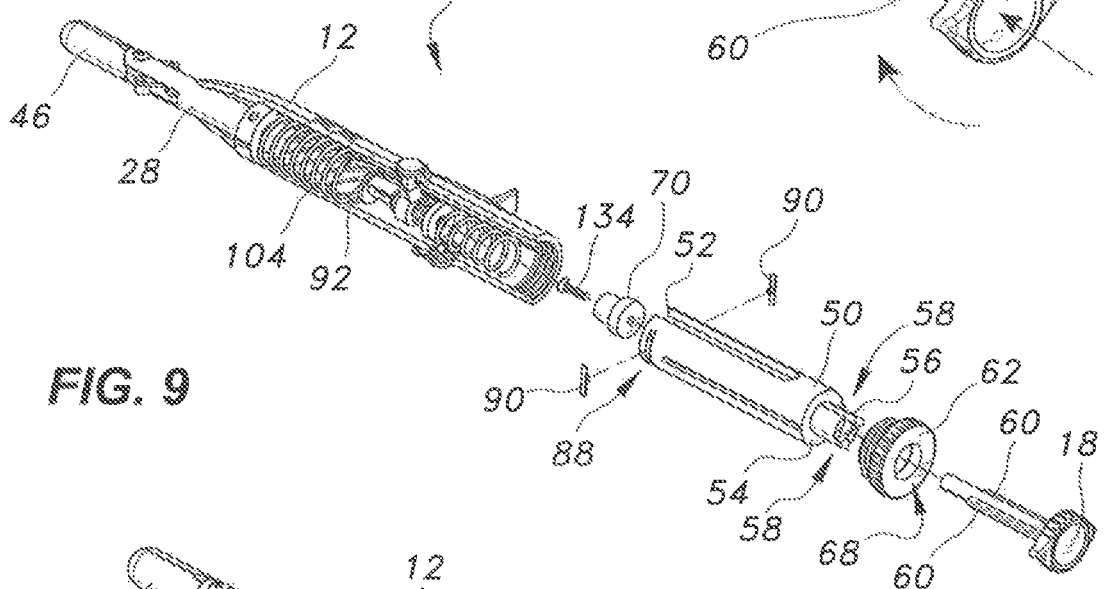
FIG. 9 is a partially exploded, partially cut-away perspective view of the surgical wire twisting tool.
Figure 10:
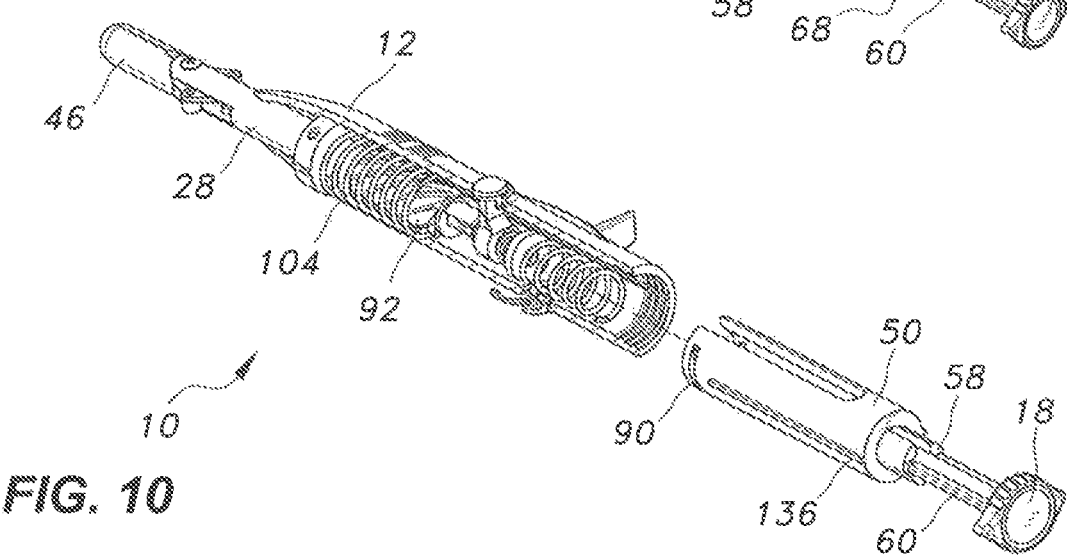
FIG. 10 is a partially exploded, partially cut-away perspective view of the surgical wire twisting tool.

As best seen in FIGS. 4 and 8-10, a hollow cylindrical guide 50, having opposed first and second ends 52, 54, respectively, may also be received within hollow housing 12. It should be understood that hollow cylindrical guide 50 is shown for exemplary purposes only and may have any suitable overall shape and relative dimensions. A guide head 56 may be formed on the second end 54 for engaging with the plunger 18. As best seen in FIG. 9, a pair of slots 58 may be formed in guide head 56 for receiving ends of a pair of rails 60 secured to rod 24 of plunger 18. The hollow cylindrical guide 50 may have one or more axial slots 136 formed therethrough for engaging with ribs or the like formed on the inner surface of hollow housing 12, thus preventing unwanted rotation of the hollow cylindrical guide 50.

When pressed down by the user, the rod 24 of plunger 18 pushes within hollow cylindrical guide 50. The hollow cylindrical guide 50 may be held in place by a cap 62 having threads 64 for engaging threads 66 formed in the interior surface of second open end 16 of hollow housing 12. It should be understood that cap 62 is shown for exemplary purposes only, and may have any suitable overall shape and relative dimensions. As shown in FIG. 9, cap 62 has a central opening 66 formed therethrough for receiving rod 24 of plunger 18.

In FIGS. 5 and 6, the hollow cylindrical guide 50 has been removed for purposes of illustration and clarity. As shown in FIGS. 4-6, first and second end caps 68, 70, respectively, are received within the hollow cylindrical guide 50, such that the first end 20 of plunger 18 contacts the second end cap 70. It should be understood that first and second end caps 68, 70 are shown for exemplary purposes only, and may each have any suitable overall shape and relative dimensions. Second end cap 70 may be held in place within hollow cylindrical guide 50 by a bolt 134 or the like. The first end cap 68 contacts the second end 40 of jaw actuating rod 36. The first and second end caps 68, 70 are elastically biased with respect to one another by a spring 72 or the like. It should be understood that helical spring 72 is shown for exemplary purposes only, and that any suitable type of elastic bias may be used. Thus, when the user pushes down on plunger 18, first end 20 of plunger 18 pushes down on second end cap 70 which, through the elastic biasing of spring 72, pushes down on first end cap 68, as shown in FIG. 6. First end cap 68 pushes down on second end 40 of jaw actuating rod 36, causing jaw actuating rod 36 to slide down through rotating member 28. This, in turn, folds four-bar linkage 44, which causes jaws 46 to close. When the user releases plunger 18, plunger 18 is pushed back upwardly by spring 72, releasing the jaws 46 to open again. As further seen in FIG. 4, first end cap 68 may have a central opening for receiving a stabilizer bolt 132 or the like.

In order to lock the jaws 46 in the closed position, a recess 74 is formed in jaw actuating rod 36, adjacent its second end 40, as best seen in FIGS. 4 and 7. A resilient clip 76 is mounted on second end 32 of rotating member 28, and when plunger 18 is pushed far enough down, resilient clip 76 engages the recess 74 to lock the actuating rod 36 in place. It should be understood that resilient clip 76 is shown for exemplary purposes only, and may have any suitable overall shape and relative dimensions. When the surgeon wishes to have the jaws 46 locked in the closed position in order to hold a surgical wire or the like, in a manner similar to locking forceps, the plunger 18 is pushed far enough down for the locking to take place.

In order for the jaw actuating rod 36 to be unlocked, thus allowing the jaws 46 to open, the user presses the jaw unlocking button 78. With reference to FIGS. 1 and 3, it should be understood that jaw unlocking button 78 is shown for exemplary purposes only, and may have any suitable overall shape and relative dimensions, as well as any suitable location with respect to hollow housing 12. As shown in FIG. 7, the jaw unlocking button 78 has an internal beveled end 80, which contacts a complementary beveled end 82 of a sliding ring 84. When jaw unlocking button 78 is pushed inwardly, sliding ring 84 is forced to slide downwardly, thus disengaging resilient clip 76 from recess 74 and unlocking the jaw actuating rod 36. In order to prevent unwanted upward movement of sliding ring 84, sliding ring 84 may be biased against first end cap 68 by a spring 130 or the like, as shown in FIG. 4. It should be understood that helical spring 130 is shown for exemplary purposes only, and that any suitable type of elastic bias may be used. With reference to FIGS. 5-7, it should be understood that sliding ring 84 is shown for exemplary purposes only, and may have any suitable overall shape and relative dimensions.

When the jaws 46 are in the closed and locked position and the surgeon wishes to cause the jaws 46 to rotate (to twist surgical wire or the like), the plunger 18 is pulled upwardly and rotated to disengage rails 60 of plunger 18 from slots 58 of guide head 56. This rotation is indicated by the solid arrow in FIG. 8. With rails 60 no longer free to slide within slots 58, the ends of rails 60 will push down on guide head 56, causing the cylindrical guide 50 to slide downward within the hollow housing 12. As shown in FIGS. 4 and 9, a pair of slots 88 are formed through cylindrical guide 50, adjacent its first end 52, for receiving a pair of substantially T-shaped engaging members 90. Engaging members 90 engage spiral grooves 92 formed in the second end 32 of rotating member 28. It should be understood that engaging members 90 are shown for exemplary purposes only, and may have any suitable overall shape and relative dimensions.

By pushing down on plunger 18, the cylindrical guide 50 is pushed down, causing the engaging members 90 to travel downwardly within spiral grooves 92, generating rotation in the rotating member 28 in one direction. Rotation of rotating member 28 causes the jaw actuating rod 36 to rotate, thus rotating jaws 46 (indicated by the dashed arrow in FIG. 8). It should be understood that spiral grooves 92 are shown for exemplary purposes only, and may have any suitable overall shape and relative dimensions.

Rotating member 28 may be received through a stabilizing ring 96, which fits snugly against the interior of hollow housing 12, thus preventing unwanted radial movement of rotating member 28. As shown in FIG. 4, an annular groove 98 may be formed substantially centrally in rotating member 28 for engaging with stabilizing ring 96, allowing free rotation of the rotating member 28 but preventing axial movement thereof. Openings 102 may be formed radially through stabilizing ring 96, as shown, for receiving pins 10, thus providing an engaging surface for reception by annular groove 98. The cylindrical guide 50 is elastically biased by spring 104 or the like. It should be understood that helical spring 104 is shown for exemplary purposes only, and that any suitable type of elastic bias may be used. Thus, when the procedure is finished, the surgeon presses jaw unlocking button 78, as described above, causing the plunger 18 to move back to its upward position and opening jaws 46. As the plunger 18 moves back upward to its original position, the plunger 18 does not engage the cylindrical guide 50. As shown in FIG. 4, an axial slot 124 may be formed in the circumferential surface of stabilizing ring 96. A corresponding engaging member may be formed on the inner surface of hollow housing 12 to prevent unwanted rotation of stabilizing ring 96.

Figure 11:
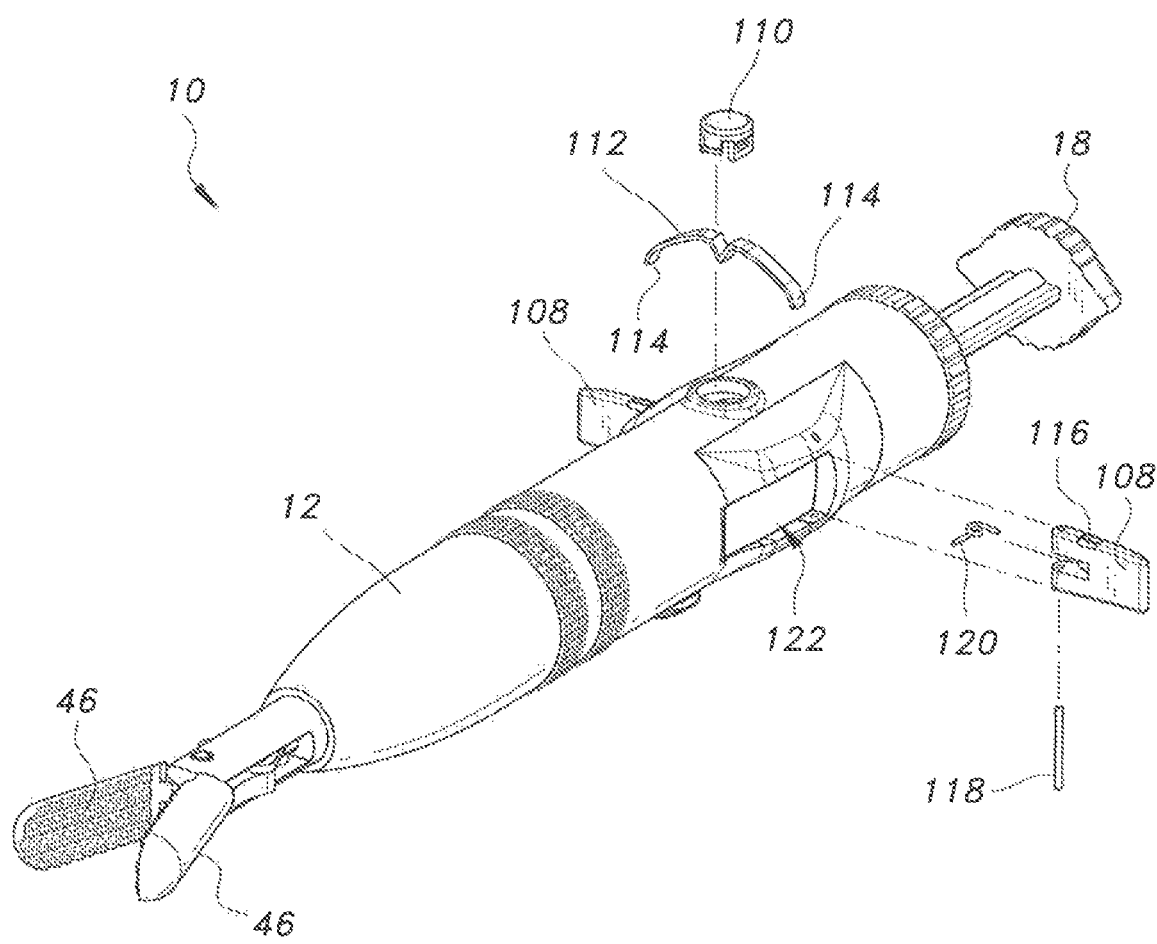
FIG. 11 is a partially exploded, perspective view of the surgical wire twisting tool.

An additional pair of collapsible wings 108 may be pivotally attached to the hollow housing 12, providing collapsible finger grips for the surgeon. As best seen in FIGS. 4 and 11, a wing release button 110 is provided in hollow housing 12 for deploying the pair of collapsible wings 108. With reference to FIG. 2, it should be understood that wing release button 110 is shown for exemplary purposes only, and may have any suitable overall shape and relative dimensions, as well as any suitable location with respect to hollow housing 12. Returning to FIGS. 4 and 11, an elastic member 112 is received within hollow housing 12, and pressing down on wing release button 110 causes the opposed ends 114 of elastic member 112 to lift, thus disengaging ends 114 from grooves 116 respectively formed in collapsible wings 108. As best seen in FIG. 11, each wing 108 may be pivotally secured to hollow housing 12 by a pivot pin 118 or the like, and is elastically biased by a spring 120 or the like. It should be understood that spring 120 is shown for exemplary purposes only, and that any suitable type of elastic bias may be used. When the surgeon wishes to collapse the wings 108, they may be folded back into compartments 122, formed in hollow housing 12, with the surgeon pushing against the resistance caused by spring 120. When wing release button 110 is disengaged, ends 114 of elastic member 112 will reengage grooves 116, thus locking the pair of collapsible wings 108 back into their collapsed position.

It is to be understood that the surgical wire twisting tool is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A surgical wire twisting tool, comprising:
   a hollow housing having opposed first and second open ends;
   a plunger having opposed first and second ends, the first end of the plunger being slidably received within the second open end of the hollow housing;
   a hollow rotating member received within the hollow housing, such that a first end of the rotating member projects through the first open end of the hollow housing;
   a jaw actuating rod having opposed first and second ends and at least partially received within the rotating member;
   a pair of jaws pivotally mounted on the first end of the jaw actuating rod;
   means for selectively opening and closing the pair of jaws;
   a hollow cylindrical guide having opposed first and second ends and being received within the hollow housing, wherein the second end of the jaw actuating rod projects through the second end of the rotating member and into the first end of the hollow cylindrical guide, the plunger being selectively slidable through the second end of the hollow cylindrical guide to drive sliding movement of the jaw actuating rod with respect to the rotating member; and
   means for selectively rotating the pair of jaws.

2. The surgical wire twisting tool as recited in claim 1, wherein the means for selectively opening and closing the pair of jaws comprise a four-bar linkage.

3. The surgical wire twisting tool as recited in claim 2, wherein a first end of the four-bar linkage is secured to the pair of jaws and is pivotally secured to the first end of the rotating member, and a second end of the four-bar linkage is pivotally secured to the first end of the jaw actuating rod.

4. The surgical wire twisting tool as recited in claim 1, wherein the plunger comprises a rod having opposed first and second ends, at least one rail being secured to the rod.

5. The surgical wire twisting tool as recited in claim 4, wherein a guide head is formed on the second end of the hollow cylindrical guide, the guide head having at least one slot formed therethrough for releasably receiving and engaging the at least one rail of the plunger.

6. The surgical wire twisting tool as recited in claim 5, further comprising first and second end caps received within the hollow cylindrical guide, the second end cap being adapted for contacting the first end of the rod of the plunger, and the first end cap being adapted for contacting the second end of the jaw actuating rod.

7. The surgical wire twisting tool as recited in claim 6, wherein the first and second end caps are elastically biased with respect to one another.

8. The surgical wire twisting tool as recited in claim 4, wherein the means for selectively rotating the pair of jaws comprise at least one engaging member mounted on the cylindrical guide for engaging at least one spiral groove formed in the second end of the rotating member, whereby the plunger selectively drives axial movement of the cylindrical guide and the at least one engaging member to generate rotational movement in the rotating member.

9. The surgical wire twisting tool as recited in claim 8, wherein the cylindrical guide is elastically biased with respect to the hollow housing.

10. The surgical wire twisting tool as recited in claim 1, further comprising means for selectively locking the pair of jaws.

11. The surgical wire twisting tool as recited in claim 10, wherein the means for selectively locking the pair of jaws comprise a resilient clip mounted on the second end of the rotating member for releasably engaging a recess formed in the jaw actuating rod.

12. The surgical wire twisting tool as recited in claim 1, further comprising a pair of collapsible wings pivotally mounted on an outer surface of the hollow housing.

13. The surgical wire twisting tool as recited in claim 12, wherein the pair of collapsible wings are received in a pair of compartments formed in the outer surface of the hollow housing when the pair of collapsible wings are in a collapsed state.

14. A surgical wire twisting tool, comprising:
a hollow housing having opposed first and second open ends;
a plunger having opposed first and second ends, the first end of the plunger being slidably received within the second open end of the hollow housing;
a hollow rotating member received within the hollow housing, such that a first end of the rotating member projects through the first open end of the hollow housing;
a jaw actuating rod having opposed first and second ends and at least partially received within the rotating member;
a pair of jaws pivotally mounted on the first end of the jaw actuating rod;
means for selectively opening and closing the pair of jaws;
a hollow cylindrical guide having opposed first and second ends and being received within the hollow housing, wherein the second end of the jaw actuating rod projects through the second end of the rotating member and into the first end of the hollow cylindrical guide, the plunger being selectively slidable through the second end of the hollow cylindrical guide to drive sliding movement of the jaw actuating rod with respect to the rotating member;
means for selectively rotating the pair of jaws; and
means for selectively locking the pair of jaws.

15. The surgical wire twisting tool as recited in claim 14, wherein the means for selectively opening and closing the pair of jaws comprise a four-bar linkage.

16. The surgical wire twisting tool as recited in claim 15, wherein a first end of the four-bar linkage is secured to the pair of jaws and is pivotally secured to the first end of the rotating member, and a second end of the four-bar linkage is pivotally secured to the first end of the jaw actuating rod.

17. The surgical wire twisting tool as recited in claim 14, wherein the plunger comprises a rod having opposed first and second ends, at least one rail being secured to the rod, and wherein a guide head is formed on the second end of the hollow cylindrical guide, the guide head having at least one slot formed therethrough for releasably receiving and engaging the at least one rail of the plunger.

18. The surgical wire twisting tool as recited in claim 17, further comprising first and second end caps received within the hollow cylindrical guide, the second end cap being adapted for contacting the first end of the rod of the plunger, and the first end cap being adapted for contacting the second end of the jaw actuating rod, the first and second end caps being elastically biased with respect to one another.

19. The surgical wire twisting tool as recited in claim 17, wherein the means for selectively rotating the pair of jaws comprise at least one engaging member mounted on the cylindrical guide for engaging at least one spiral groove formed in the second end of the rotating member, whereby the plunger selectively drives axial movement of the cylindrical guide and the at least one engaging member to generate rotational movement in the rotating member, the cylindrical guide being elastically biased with respect to the hollow housing.

20. The surgical wire twisting tool as recited in claim 14, wherein the means for selectively locking the pair of jaws comprise a resilient clip mounted on the second end of the rotating member for releasably engaging a recess formed in the jaw actuating rod.

* * * * *